(12) United States Patent
Gupta et al.

(10) Patent No.: US 10,113,018 B2
(45) Date of Patent: Oct. 30, 2018

(54) SHAPE CONTROLLED PRO-CATALYST AND A PROCESS FOR PREPARING THE SAME

(71) Applicant: Reliance Industries Limited, Mumbai (IN)

(72) Inventors: Virendrakumar Gupta, Navi Mumbai (IN); Sanjay Govindbhai Chauhan, Surat (IN); Hiren Manojkumar Bhajiwala, Surat (IN); Shakil Shabbir Sayyed, Latur (IN); Suketu Vakil, Mumbai (IN)

(73) Assignee: Reliance Industries Limited, Mumbai (IN)

( * ) Notice: Subject to any disclaimer, the term of this patent is extended or adjusted under 35 U.S.C. 154(b) by 0 days.

(21) Appl. No.: 15/312,315

(22) PCT Filed: May 22, 2015

(86) PCT No.: PCT/IB2015/053777
§ 371 (c)(1),
(2) Date: Nov. 18, 2016

(87) PCT Pub. No.: WO2015/177764
PCT Pub. Date: Nov. 26, 2015

(65) Prior Publication Data
US 2017/0081438 A1    Mar. 23, 2017

(30) Foreign Application Priority Data

May 22, 2014 (IN) .......................... 1720/MUM/2014

(51) Int. Cl.
*C08F 4/06* (2006.01)
*C08F 4/70* (2006.01)
(Continued)

(52) U.S. Cl.
CPC ............ *C08F 110/02* (2013.01); *C07C 31/30* (2013.01); *C07F 7/006* (2013.01); *C08F 10/00* (2013.01)

(58) Field of Classification Search
CPC ........ C08F 110/02; C08F 10/00; C08F 4/651; C08F 4/76; C08F 4/6543; C08F 4/6545;
(Continued)

(56) References Cited

U.S. PATENT DOCUMENTS 4,728,705 A    3/1988   Nestlerode et al.
5,225,385 A    7/1993   Chadwick et al.
(Continued)

FOREIGN PATENT DOCUMENTS

WO    2005/030815 A1    4/2005
WO    2005/044873 A1    5/2005
WO    2012/007963 A2    1/2012

OTHER PUBLICATIONS

International Search Report issued in corresponding application No. PCT/IB2015/053777 dated Aug. 31, 2015 (3 pages).
(Continued)

*Primary Examiner* — William K Cheung
(74) *Attorney, Agent, or Firm* — Osha Liang LLP

(57) ABSTRACT

The present disclosure relates to a single-pot process for the preparation of a shape controlled pro-catalyst. The process comprises the steps of i. reacting at least one alkanol with magnesium metal using at least one modifier and optionally, at least one solvent resulting in evolution of hydrogen gas, increasing the evolution of the hydrogen gas in a controlled manner by increasing the temperature in a graded manner to 100° C. to obtain a mass, and ii. subjecting the mass to drying to obtain a free flowing procatalyst.

7 Claims, 3 Drawing Sheets

1a

1b

1c

Figure 1:
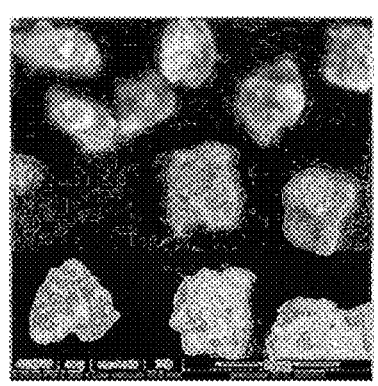
Figure 1:
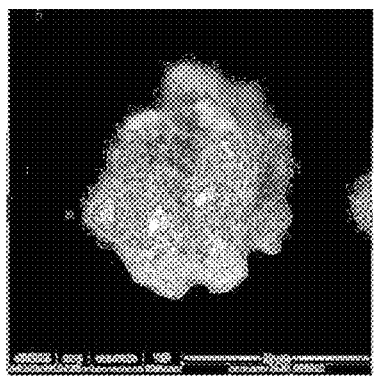
Figure 1:
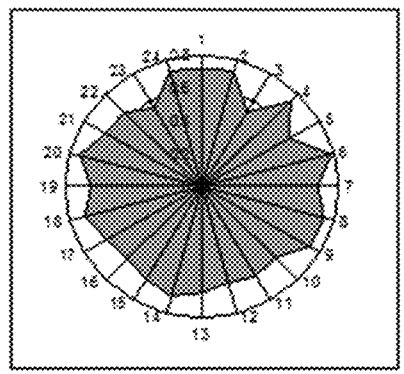

(51) Int. Cl.
*C08F 110/02* (2006.01)
*C07C 31/30* (2006.01)
*C07F 7/00* (2006.01)
*C08F 10/00* (2006.01)

(58) Field of Classification Search
CPC ........ C07C 31/30; C07F 7/006; B01J 27/138; B01J 31/02; B01J 35/08
USPC .......................... 526/123.3; 502/8, 118, 125
See application file for complete search history.

(56) References Cited

U.S. PATENT DOCUMENTS

| | | |
|---|---|---|
| 5,498,770 A | 3/1996 | Hosaka et al. |
| 5,556,820 A | 9/1996 | Funabashi et al. |
| 6,297,188 B1 | 10/2001 | Schork et al. |
| 2004/0266609 A1 | 12/2004 | Tanase et al. |
| 2006/0052237 A1* | 3/2006 | Spaether ................ C08F 10/00 502/115 |
| 2008/0281059 A1 | 11/2008 | Tanase et al. |
| 2009/0203857 A1 | 8/2009 | Tanase et al. |
| 2011/0054129 A1 | 3/2011 | Gupta et al. |

OTHER PUBLICATIONS

Written Opinion of the International Searching Authority issued in corresponding application No. PCT/IB2015/053777 dated Aug. 31, 2015 (6 pages).

* cited by examiner

3a

3b

3c

SHAPE CONTROLLED PRO-CATALYST AND A PROCESS FOR PREPARING THE SAME

This application is a National Stage Application under 35 U.S.C. § 371 of PCT Application No. PCT/IB2015/053777 filed on May 22, 2015, which claims priority under 35 U.S.C. § 365 of India Patent Application Number 1720/MUM/2014, filed on May 22, 2014. The disclosures of the PCT Application, and the India Patent Application are incorporated by reference herein in their entireties.

FIELD

The present disclosure relates to a shape controlled pro-catalyst and a process for the preparation thereof. The present disclosure also relates to a process for the preparation of polyethylene using a shape controlled pro-catalyst.

BACKGROUND

It is known that the monomers can be polymerized by using a catalyst system comprising: a compound of a transition metal such as titanium in the trivalent or tetravalent state, magnesium ethoxide as a support material and a co-catalyst of the organo-metallic type, most frequently an organo-aluminum compound.

Although these catalytic systems are active they sometimes result in the formation of polymers containing transition metal more than 100 parts per million by weight. For most of the applications of such polymers, it is essential to remove such catalytic residues by a special treatment.

It is also known that it is possible to increase the catalytic activity of a catalyst by pre-activation. This pre-activation treatment involves contacting the transition metal compound with magnesium and one or more alkyl halides. The pre-activation step results in a catalyst which produces polymers having acceptable physical characteristics. Further, the polymers obtained by using a pre-activated catalyst are capable of being processed by injection molding or extrusion. However, polymers obtained by using pre-activated catalysts have unacceptable residues, which need to be removed.

Conventional magnesium-titanium type Ziegler-Natta catalysts use non-morphological magnesium ethoxide precursors of 700-800 micron size. The catalysts produced using these precursors result in irregular shaped particles. Also, the polymers produced using these catalysts possess particles of irregular shape, low bulk density and a broad particle size distribution.

Shape regularity and size distribution of polymers are dependent on shape and size of the catalyst particles as well as on the components from which the catalyst particles are synthesized. Polymers having regular shape and narrow particle size distribution are desirable for good flowability during extrusion. Several attempts have been made to prepare a catalyst system which is capable of producing polymers having regular shape, narrow particle size distribution and high molecular weight.

WO2005/044873 suggests a method for synthesizing spherical magnesium alkoxide particles by reacting magnesium with alcohol mixture in the presence of iodine at a temperature below the boiling point of the mixture.

US2011/0054129A1 suggests a process for the synthesis of spheroidal magnesium alkoxide particles by reacting magnesium metal, in the presence of iodine, with a mixture of alcohols.

US20040266609 suggests a process for the preparation of a pro-catalyst. In the process, magnesium metal and ethanol in the presence of iodine are heated to obtain magnesium ethoxide. The magnesium ethoxide is then treated with silicon tetrachloride, di-n-butyl phthalate and titanium tetrachloride, and stirred at 125° C. to obtain the pro-catalyst.

US20090203857, US20110054129, U.S. Pat. No. 5,556,820, WO2012007963, US20080281059 and U.S. Pat. No. 5,498,770 suggest a process for the preparation of magnesium alkoxide using magnesium metal and at least one alkanol in the presence of iodine. The magnesium alkoxide obtained is then used for the preparation of a pro-catalyst for Ziegler-Natta catalyst.

However, the spherical magnesium alkoxide particles synthesized by the method of the above processes are frangible and do not retain their morphology or particle size during the synthesis of the pro-catalyst, especially when the pro-catalyst synthesis is carried out on a large scale. Further, the particle size distribution of the magnesium alkoxide particles synthesized by the above mentioned processes need improvement.

The only process that prepares magnesium alkoxide from magnesium metal and alkanol in the absence of iodine is disclosed in U.S. Pat. No. 6,297,188. However, this process suffers from a drawback that only 40 w % of the coarse grains have a screening fraction of ≤500 μm.

Accordingly, there is a need for a process for preparing a shape controlled magnesium ethoxide that retains its shape not only during the synthesis of the pro-catalyst but also during the preparation of the Ziegler-Natta catalyst and the polymerization of monomers.

Objects

Some of the objects of the present disclosure, which at least one embodiment herein satisfies, are as follows:

It is an object of the present disclosure to provide a simple and safe process for the preparation of a shape controlled pro-catalyst.

It is another object of the present disclosure to provide a process for the preparation of a shape controlled pro-catalyst which obviates the use of iodine.

It is still another object of the present disclosure to provide a process for the preparation of a stable and infrangible shape controlled pro-catalyst.

It is yet another object of the present disclosure to provide a process for the preparation of a shape controlled pro-catalyst which is amenable on large scale.

It is a further object of the present disclosure to provide a catalyst comprising a shape controlled pro-catalyst.

It is still a further object of the present disclosure to provide a process for the polymerization of a monomer using the pro-catalyst of the present disclosure.

Other objects and advantages of the present disclosure will be more apparent from the following description which is not intended to limit the scope of the present disclosure.

SUMMARY

In accordance with one aspect of the present disclosure there is provided a single-pot process for the preparation of a shape controlled pro-catalyst. The single-pot process comprises reacting at least one alkanol with magnesium metal using at least one organic modifier, inorganic modifier or a combination thereof and optionally, at least one solvent. During the reaction hydrogen gas is evolved. The rate of evolution of hydrogen gas is increased in a controlled manner by increasing the temperature in a graded manner to 100° C. to obtain a mass containing the pro-catalyst which is then dried to provide a free flowing pro-catalyst. The pro-catalyst has a controlled shape and the particle size ranges between 10 to 50μ.

The pro-catalyst is mixed with at least one aluminium base co-catalyst and optionally, with at least one external donor to obtain a catalyst which is used for the polymerization of ethylene monomer into polyethylene.

BRIEF DESCRIPTION OF THE ACCOMPANYING DRAWINGS

Figure 2:
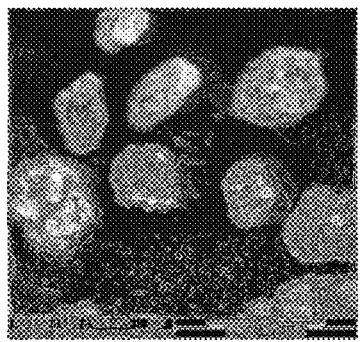
Figure 2:
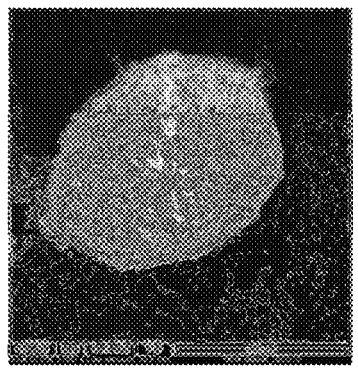
Figure 2:
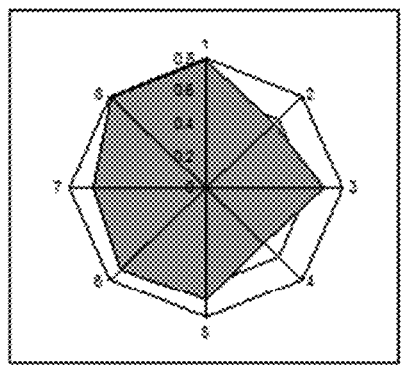
Figure 3:
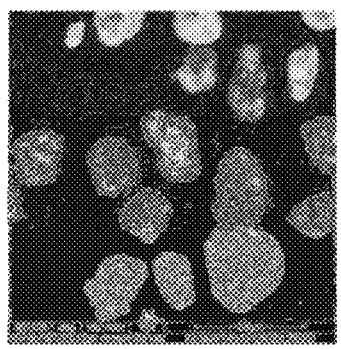
Figure 3:
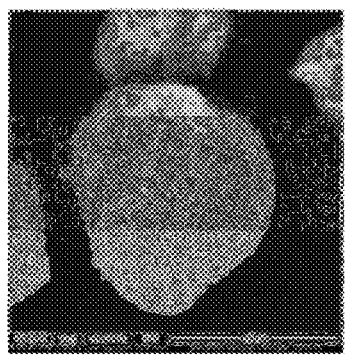
Figure 3:
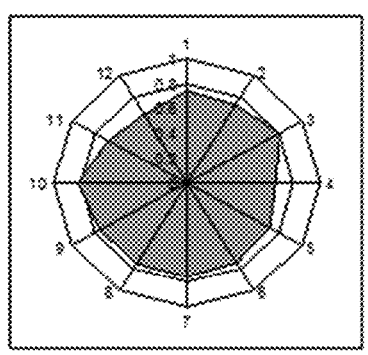

The disclosure will now be explained in relation to the non-limiting accompanying drawings, in which:

FIGS. 1a and 1b—illustrate the morphology of the pro-catalyst obtained in example 1, FIG. 1c—illustrates the circularity of the pro-catalyst obtained in example 1, FIGS. 2a and 2b—illustrate the morphology of the pro-catalyst obtained in example 1.2, FIG. 2c—illustrates the circularity of the pro-catalyst obtained in example 1.2, FIGS. 3a and 3b—illustrate the morphology of the pro-catalyst obtained in example 1.4, and FIG. 3c—illustrates the circularity of the pro-catalyst obtained in example 1.4.

DETAILED DESCRIPTION

In one aspect of the present disclosure there is provided a single-pot process for the preparation of a shape controlled pro-catalyst.

The pro-catalyst is prepared by mixing magnesium metal with at least one alkanol at a temperature ranging from 5° C. to 40° C. with constant stiffing. To the mixture obtained at least one modifier and optionally at least one solvent is added which results in the evolution of hydrogen gas. The hydrogen gas evolution rate is increased by increasing the temperature in a step wise manner to 100° C. to obtain the pro-catalyst. The pro-catalyst obtained is then dried in the presence of an inert atmosphere to obtain a free-flowing pro-catalyst. The reaction is exothermic. During experimentation, it was found that the fast reaction rate due to the exothermic nature of the reaction leads to the generation of fines and irregular morphology of the resulting pro-catalyst. Therefore, to retain the morphology and shape of the particles of the procatalyst and to avoid the generation of fines, the reaction is carried out at a controlled temperature. The temperature of the exothermic reaction may be controlled by any manner known to a person skilled in the art. The reaction is initiated at a temperature ranging between 5 and 40° C. Due to the exothermic nature of the reaction, the temperature of the reaction mixture rises. The temperature of the reaction mixture is allowed to increase gradually and in a controlled manner by circulating cool water and maintaining the reaction at a temperature in the range of 60 to 100° C. to obtain the shape controlled pro-catalyst. Hydrogen evolved during the reaction is vented off through vent condenser.

The process of the present disclosure is characterized in that the iodine or iodine containing compound is not used as an initiator for the preparation of the shape controlled pro-catalyst. The absence of iodine leads to the formation of stable and infrangible spheroidal magnesium alkoxide. Further, the spheroidal magnesium alkoxide formed in the process of the present disclosure retains its shape during the application in the preparation of Ziegler-Natta catalyst and the polymerization of the monomers. Further, the pro-catalyst obtained by the process has a particle size in the range of 10 and 50μ.

The alkanol used for the purpose of the present disclosure is selected from the group consisting of methanol, ethanol, propanol, isopropanol, butanol, isobutanol and t-butanol.

The modifier is selected from the group consisting of organic modifier and inorganic modifier. The organic modifier used in the preparation of the pro-catalyst is selected from the group consisting of ethyl benzoate, di-isobutyl phthalate and 9, 9-bis(methoxymethyl)fluorine. The inorganic modifier is at least one transition metal tetrahalide selected from the group consisting of titanium tetrachloride ($TiCl_4$), vanadium tetrachloride ($VCl_4$), silicon tetrachloride ($SiCl_4$), zirconium tetrachloride ($ZrCl_4$) and hafnium tetrachloride ($HfCl_4$).

The solvent used for the purpose of the present disclosure may be aliphatic or aromatic solvent.

In one embodiment the pro-catalyst obtained by the process of the present disclosure is further mixed with at least one aluminium based co-catalyst to obtain a catalyst. In another embodiment the pro-catalyst obtained by the process of the present disclosure is further mixed with at least one aluminium based co-catalyst and at least one external donor to obtain a catalyst. The external donor useful for the purpose of this invention is selected from the group consisting of an organo-silane compound such as cyclohexyl methyl di-methoxy silane and aromatic ester such as p-isopropoxy ethyl benzoate.

In yet another aspect of the present disclosure there is provided a pro-catalyst. The pro-catalyst comprises spheroidal magnesium alkoxide complexed with at least one modifier. The particle size of the pro-catalyst of the present disclosure is in the range of 10 and 50μ. Further, the procatalyst of the present disclosure is essentially devoid of iodine.

In yet another aspect of the present disclosure there is provided the use of the pro-catalyst in the preparation of a catalyst. The catalyst comprises the pro-catalyst of the present disclosure, at least one aluminium based co-catalyst and optionally, at least one external donor.

In still another aspect of the present disclosure there is provided the use of pro-catalyst of the present disclosure in the process for the preparation of polyethylene. The process involves polymerizing an ethylene monomer using the catalyst which comprises the pro-catalyst of the present disclosure. The polyethylene obtained by the process of the present disclosure possesses a molecular weight in the range of 1 to 60 Lacs and has a particle size in the range of 200 to 300μ.

The present disclosure is further described in the light of the following non-limiting examples which are set forth for illustration purpose only and are not to be construed for limiting the scope of the disclosure.

EXAMPLES

Example 1

Synthesis of a Titanium tetrachloride-Zirconium Tetrachloride Based Pro-Catalyst:

In a three neck 500 ml jacketed glass reactor, 125 ml of ethanol was taken at 5° C. under $N_2$ atm to which 5 gm of magnesium metal were added with constant stiffing of 150 rpm. To this 2.5 ml of $TiCl_4$ and 3.5 gm $ZrCl_4$ were added along with 25 ml ethanol slowly at a constant rate of 2 ml/min. After addition of $TiCl_4$ and $ZrCl_4$, evolution of H2 with bubbles was observed (this indicated the start of the reaction).

The rate of hydrogen evolution was monitored visually and the temperature was increased in a step wise manner 5° C. to 15° C. after 1.5 hrs. From 15 to 65° C., 10° C. temperature was raised every 1 hr. From 65° C. to 80° C., the temperature of the reaction was controlled by cool water flow in the jacket side. Whenever the hydrogen evolution ceased or decreased, the temperature was increased by 5° C. to continue the reaction. The reaction mixture was refluxed for one hour at 80° C. and once the hydrogen evolution ceased, the temperature was further increased to 100° C. to remove un-reacted ethanol from the reactor. The pro-catalyst obtained was subjected to drying at about 110° C. under the flow of nitrogen to obtain a free flowing powder.

The exact process parameters are shown in the following Table-1. The morphology of the procatalyst is depicted in FIGS. 1a and 1b and the circularity of the pro-catalyst is depicted in FIG. 1c.

Example 2

The pro-catalyst was synthesized using $TiCl_4$ and $ZrCl_4$ as reported in example 1 except the quantity of $TiCl_4$, $ZrCl_4$ was altered. The process parameters and the quantity of the reaction components employed for this example are given in Table 1.

Example 3

The pro-catalyst was synthesized using $HfCl_4$ instead of $TiCl_4$ and $ZrCl_4$ reported in example 1. The process parameters and the quantity of the reaction components employed for this example are given in Table 1. The morphology of the pro-catalyst is depicted in FIGS. 2a and 2b and the circularity of the pro-catalyst is depicted in FIG. 2c.

Example 4

The pro-catalyst was synthesized using $ZrCl_4$ as a modifier instead of a mixture of $TiCl_4$ and $ZrCl_4$ reported in example 1. The process parameters and the quantity of the reaction components employed for this example are given in Table 1.

Example 5

The pro-catalyst was synthesized using benzoyl chloride as a modifier instead of $TiCl_4$ and $ZrCl_4$ reported in example 1. The process parameters and the quantity of the reaction components employed for this example are given in Table 1.

TABLE 1

Process Parameters of Example 1

| Experiment Detail | Mg metal Qty (gm) | $TiCl_4$ Qty (ml) | $HfCl_4$ Qty (gm) | $ZrCl_4$ Qty (gm) | BzCl Qty (ml) | Ethanol Qty (ml) | Temp. (° C.) From-To | Total Time (Hrs) | Agitator Speed (rpm) | Mg:EtOH:Ti:Zr (Mole ratio) |
|---|---|---|---|---|---|---|---|---|---|---|
| Example 1 | 5 | 2.5 | — | 3.5 | — | 150 | 5-100 | 6-8 | 150 | 1:12.5:0.11:0.072 |
| Example 2 | 5 | 5.0 | — | 0.35 | — | 150 | 5-110 | 6-8 | 150 | 1:12.5:0.22:0.072 |
| Example 3 | 10 | — | 0.96 | — | — | 150 | 5-110 | 6-8 | 400 | 1:2.6:0.0072 |
| Example 4 | 10 | — | — | 0.70 | — | 150 | 5-110 | 6-8 | 400 | 1:6.3:0.0072 |
| Example 5 | 10 | — | — | — | 0.35 | 150 | 5-110 | 6-8 | 400 | 1.0:2.5:0.0072 |

The morphology and sphericity (or circularity) of pro-catalysts obtained in Example 1 to 5 were determined by scanning electron microscopy. The sphericity/circularity was measured from the area covered by a particle under the SEM image through image analysis software.

Circularity (sphericity) of a particle is: (Area of 2 dimensional particle image)/(Area of circle having same parameter as the particle)

Similarly many particle images were considered for the above and then the average was taken as the overall sphericity of the material.

The composition analysis of pro-catalysts is provided in Table 2

TABLE 2

Compositional and Morphology of pro-catalysts of Example 1 to 5

| Pro-catalyst of Example No | Modifier | Mg (wt %) | Ti (wt %) | Cl (wt %) | Modifier (M1) (wt %) | Modifier (M2) (wt %) | Ethoxy (%) | D Mean (μ) | Circularity |
|---|---|---|---|---|---|---|---|---|---|
| 1 | M1-$TiCl_4$-M2-$ZrCl_4$ | 19.6 | 5.2 | 1.0 | 0.1 | 0.1 | 75.6 | 29 | 0.69 |
| 2 | M1-$TiCl_4$-M2-$ZrCl_4$ | 21.2 | 5.2 | 0.61 | 0.1 | 0.1 | 75.9 | 26 | |

TABLE 2-continued

Compositional and Morphology of pro-catalysts of Example 1 to 5

| Pro-catalyst of Example No | Modifier | Mg (wt %) | Ti (wt %) | Cl (wt %) | Modifier (M1) (wt %) | Modifier (M2) (wt %) | Ethoxy (%) | D Mean (μ) | Circularity |
|---|---|---|---|---|---|---|---|---|---|
| 3 | M1-HfCl₄ | 19.4 | — | 1.03 | 1.0 | — | 75.8 | 38 | 0.67 |
| 4 | M1-ZrCl₄ | 19.6 | — | 1.0 | 0.1 | — | 75.8 | 47 | |
| 5 | Benzoyl Chloride (% in-situ formed modifier not determined) | 22.8 | — | 0.55 | — | — | 75.6 | 36 | 0.72 |

Polymerization Performance and Product Characterization:

The ethylene slurry polymerization was carried out in 450 ml SS high pressure reactor at 400 rpm using triethyl aluminium as co catalyst, n-hexane as a solvent and at 6.0 kg/cm2 ethylene pressure for 120 minutes at 80° C. temperature.

The polymer obtained after cooling the reactor was washed, dried and quantified for determination of catalyst activity. The polymer was also characterized for Viscosity Avg. Molecular wt, APS, BD and Thermal characteristics. The morphology of polymer resin is determined by scanning electron microscopy.

Example 6

Ethylene polymerization using $TiCl_4$—$ZrCl_4$ based pro-catalyst obtained in example 1 with triethylaluminium (TEAL) as co-catalyst with and without hydrogen.

Process conditions: Temp: 80° C., Pressure: 6 kg/cm², Al/Ti: 10, catalyst: 250 mg. Reaction Time: 2hrs. The analysis of the polymer is provided in Table 3

TABLE 3

Polymerization performance of TiCl4-ZrCl4 based pro-catalyst used in Example-6

| Pro-cat | H₂ mmol | Al/Ti | Al/D | Activity (g PE/g cat) | Molecular wt. (Mv) Million | APS (μ) | BD (g/cc) | Tm (° C.) | Tc (° C.) | % Crystanality |
|---|---|---|---|---|---|---|---|---|---|---|
| 1 | 0 | 10 | — | 34 | 2.7 | 262 | 0.31 | 139.4 | 112.1 | 48.24 |
| | 9.5 | 10 | — | 41 | 0.7 | 243 | 0.32 | 141.7 | 115.0 | 49.03 |

APS: Average Particle Size
BD: Bulk Density
Tm: Melting Temperature
Tc: Crystallization Temperature Technical Advancement and Economic Significance:
The present disclosure has the following advantages:
The present disclosure provides a process for the synthesis of superior catalyst having narrow particle size distribution with morphological particles,
The polymer obtained by the process of the present disclosure possesses good particle size distribution of resin, better flowability, improved morphology and bulk density, and The catalyst of the present disclosure has the potential to prepare ultrahigh density polyethylene.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

The use of the expression "at least" or "at least one" suggests the use of one or more elements or ingredients or quantities, as the use may be in the embodiment of the disclosure to achieve one or more of the desired objects or results.

Any discussion of documents, acts, materials or the like that has been included in this specification is solely for the purpose of providing a context for the disclosure. It is not to be taken as an admission that any or all of these matters form a part of the prior art base or were common general knowledge in the field relevant to the disclosure as it existed anywhere before the priority date of this application.

The numerical values mentioned for the various physical parameters, dimensions or quantities are only approximations and it is envisaged that the values higher/lower than the numerical values assigned to the parameters, dimensions or quantities fall within the scope of the disclosure, unless there is a statement in the specification specific to the contrary.

While considerable emphasis has been placed herein on the specific features of the preferred embodiment, it will be appreciated that many additional features can be added and that many changes can be made in the preferred embodiment without departing from the principles of the disclosure. These and other changes in the preferred embodiment of the disclosure will be apparent to those skilled in the art from the disclosure herein, whereby it is to be distinctly understood that the foregoing descriptive matter is to be interpreted merely as illustrative of the disclosure and not as a limitation.

The invention claimed is:

1. A single-pot process for the preparation of a shape controlled pro-catalyst; said process comprising the following steps:
   a. reacting at least one alkanol with magnesium metal using at least one modifier and at least one solvent resulting in evolution of hydrogen gas; increasing the evolution of hydrogen gas in a controlled manner by increasing the temperature in a graded manner to 100° C. to obtain a mass, and
   b. subjecting the mass to drying to obtain a free flowing pro-catalyst.

2. The process as claimed in claim 1, wherein the alkanol is selected from the group consisting of methanol, ethanol, propanol, isopropanol, butane, isobutanol and t-butanol.

3. The process as claimed in claim 1, wherein the modifier is selected from the group consisting of organic modifier and inorganic modifier.

4. The process as claimed in claim 3, wherein organic modifier is at least one selected from the group consisting of ethyl benzoate, di-isobutyl phthalate and 9, 9-bis (methoxymethyl) fluorine.

5. The process as claimed in claim 3, wherein the inorganic modifier is selected from the group consisting of titanium tetrachloride ($TiCl_4$), vanadium tetrachloride ($VCl_4$), silicon tetrachloride ($SiCl_4$), zirconium tetrachloride ($ZrCl_4$) and hafnium tetrachloride ($HfCl_4$).

6. The process as claimed in claim 1, wherein the solvent is selected from the group consisting of aliphatic and aromatic solvent.

7. The process as claimed in claim 1, wherein the shape controlled pro-catalyst has a particle size in the range of 10 to 50 μ.

* * * * *